United States Patent
Kim et al.

(10) Patent No.: US 9,289,146 B2
(45) Date of Patent: Mar. 22, 2016

(54) APPARATUS AND METHOD FOR MEASURING BIOLOGICAL SIGNAL WITH MULTIPLE UNIT MEASURERS

(75) Inventors: Youn-ho Kim, Hwaseong-si (KR); Jeong-whan Lee, Suwon-si (KR); Kun-soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 291 days.

(21) Appl. No.: 13/166,880

(22) Filed: Jun. 23, 2011

(65) Prior Publication Data

US 2012/0190994 A1 Jul. 26, 2012

(30) Foreign Application Priority Data

Jan. 26, 2011 (KR) .................. 10-2011-0007882

(51) Int. Cl.
 *A61B 5/0404* (2006.01)
 *A61B 5/0402* (2006.01)
 *A61B 5/04* (2006.01)
 *G06F 19/00* (2011.01)

(52) U.S. Cl.
 CPC ............. *A61B 5/0404* (2013.01); *A61B 5/0402* (2013.01); *A61B 2560/0443* (2013.01); *G06F 19/3406* (2013.01)

(58) Field of Classification Search
 CPC .... A61B 5/04; A61B 5/04011; A61B 5/0402; A61B 5/04021; A61B 5/04028; A61B 5/0456; A61B 5/0404
 USPC .................................................. 600/509, 547
 See application file for complete search history.

(56) References Cited

U.S. PATENT DOCUMENTS

| 4,205,386 | A  | * | 5/1980  | Ruszala et al. ..................... 708/8 |
| 5,058,598 | A  |   | 10/1991 | Nicklas et al. |
| 5,184,620 | A  | * | 2/1993  | Cudahy et al. ................ 600/382 |
| 5,224,479 | A  | * | 7/1993  | Sekine .......................... 600/389 |
| 5,740,811 | A  | * | 4/1998  | Hedberg et al. ............... 600/510 |
| 5,755,739 | A  | * | 5/1998  | Sun et al. ........................ 607/14 |
| 5,782,238 | A  | * | 7/1998  | Beitler .......................... 600/372 |
| 5,868,671 | A  | * | 2/1999  | Mahoney ...................... 600/382 |
| 5,938,597 | A  | * | 8/1999  | Stratbucker ................... 600/382 |
| 6,055,448 | A  | * | 4/2000  | Anderson et al. ............. 600/372 |
| 6,219,569 | B1 | * | 4/2001  | Kelly et al. .................... 600/386 |
| 6,327,487 | B1 | * | 12/2001 | Stratbucker ................... 600/382 |
| 6,400,975 | B1 | * | 6/2002  | McFee .......................... 600/372 |

(Continued)

FOREIGN PATENT DOCUMENTS

| JP | 2002-282230 | 10/2002 |
| JP | 2002-306438 | 10/2002 |

(Continued)

*Primary Examiner* — Christopher A Flory
(74) *Attorney, Agent, or Firm* — NSIP Law

(57) ABSTRACT

A biological signal measuring apparatus is provided. The biological signal measuring apparatus includes a first unit measurer configured to measure a first biological signal of a subject based on an electrical characteristic difference between first electrodes contacting the skin of the subject, and a second unit measurer configured to measure a second biological signal of the subject based on an electrical characteristic difference between second electrodes contacting the skin of the subject at positions different from positions of the first electrodes. A plurality of unit measurers including at least the first unit measurer and the second unit measurer are arranged based on characteristics of contact parts of the first and second electrodes.

11 Claims, 9 Drawing Sheets

(56) References Cited

U.S. PATENT DOCUMENTS

| | | | |
|---|---|---|---|
| 6,453,186 B1 * | 9/2002 | Lovejoy et al. | 600/386 |
| 6,546,285 B1 * | 4/2003 | Owen et al. | 607/5 |
| 6,560,473 B2 * | 5/2003 | Dominguez | 600/382 |
| 6,847,836 B1 * | 1/2005 | Sujdak | 600/382 |
| 6,901,285 B2 * | 5/2005 | Schreck | 600/509 |
| 7,197,357 B2 * | 3/2007 | Istvan et al. | 600/509 |
| 7,245,974 B2 * | 7/2007 | Dupelle et al. | 607/142 |
| 7,266,405 B1 * | 9/2007 | Alroy et al. | 600/386 |
| 7,444,177 B2 * | 10/2008 | Nazeri | 600/382 |
| 7,558,621 B2 | 7/2009 | Blakley | |
| 7,672,721 B2 * | 3/2010 | Chirife et al. | 607/9 |
| 7,751,872 B2 * | 7/2010 | Clayman | 600/509 |
| 7,769,465 B2 * | 8/2010 | Matos | 607/60 |
| 7,933,642 B2 * | 4/2011 | Istvan et al. | 600/509 |
| 8,050,733 B2 * | 11/2011 | Rytky | 600/388 |
| 8,135,462 B2 * | 3/2012 | Owen et al. | 607/6 |
| 8,180,457 B2 * | 5/2012 | Matos | 607/60 |
| 8,185,199 B2 * | 5/2012 | Lisogurski et al. | 607/9 |
| 2002/0082491 A1 * | 6/2002 | Nissila | 600/391 |
| 2003/0187363 A1 * | 10/2003 | Alroy | 600/509 |
| 2004/0039419 A1 * | 2/2004 | Stickney et al. | 607/5 |
| 2004/0116969 A1 * | 6/2004 | Owen et al. | 607/6 |
| 2005/0197586 A1 * | 9/2005 | Pearlman | 600/509 |
| 2006/0149157 A1 * | 7/2006 | Weil et al. | 600/518 |
| 2008/0208273 A1 * | 8/2008 | Owen et al. | 607/6 |
| 2009/0048528 A1 * | 2/2009 | Hopenfeld et al. | 600/516 |
| 2009/0264782 A1 * | 10/2009 | Pearlman | 600/509 |
| 2010/0056938 A1 * | 3/2010 | Pearlman | 600/509 |
| 2010/0249623 A1 * | 9/2010 | Makdissi | 600/509 |
| 2010/0256699 A1 * | 10/2010 | Makdissi | 607/5 |
| 2012/0035485 A1 * | 2/2012 | Owen et al. | 600/479 |
| 2012/0035676 A1 * | 2/2012 | Owen et al. | 607/6 |
| 2013/0060148 A1 * | 3/2013 | Owen et al. | 600/479 |
| 2014/0058469 A1 * | 2/2014 | Owen et al. | 607/6 |
| 2014/0073894 A1 * | 3/2014 | Makdissi | 600/374 |
| 2015/0011903 A1 * | 1/2015 | Makdissi | 600/509 |

FOREIGN PATENT DOCUMENTS

| | | |
|---|---|---|
| JP | 2006-141813 | 6/2006 |
| KR | 1998-0008168 | 4/1998 |

* cited by examiner

APPARATUS AND METHOD FOR MEASURING BIOLOGICAL SIGNAL WITH MULTIPLE UNIT MEASURERS

CROSS-REFERENCE TO RELATED APPLICATIONS

This application claims the benefit of Korean Patent Application No. 10-2011-0007882, filed on Jan. 26, 2011, in the Korean Intellectual Property Office, the entire disclosure of which is incorporated herein by reference for all purposes.

BACKGROUND

1. Field

The following disclosure relates to an apparatus and method for measuring a biological signal.

2. Description of the Related Art

As interest in U-health increases, a demand for technologies that monitor and analyze vital signs of a patient during the patient's everyday life also increases. Such application technologies include 1) electrocardiogram (ECG) measurement modules using fiber-type electrodes and 2) wrist-type, globe-type, or ring-type heartbeat detection modules. These application technologies relates to miniaturization, usability with a combination of wired and wireless communication schemes, and portability.

However, it is beneficial for the application technologies 1) to provide vital signs to individuals so that they may be interested in their own health and 2) to also directly provide the vital signs to doctors in clinics as parameters to allow health states of the individuals to be efficiently checked. Therefore, a technology for accurately detecting vital signs to be clinically used is important.

SUMMARY

Provided are an apparatus and method for measuring a biological signal.

Provided is a computer-readable recording medium storing a computer-readable program for executing the method.

According to an aspect, a biological signal measuring apparatus is provided. The biological signal measuring apparatus includes a first unit measurer configured to measure a first biological signal of a subject based on an electrical characteristic difference between first electrodes contacting the skin of the subject, and a second unit measurer configured to measure a second biological signal of the subject based on an electrical characteristic difference between second electrodes contacting the skin of the subject at positions different from positions of the first electrodes. A plurality of unit measurers including at least the first unit measurer and the second unit measurer are arranged based on characteristics of contact parts of the first and second electrodes.

The biological signal measuring apparatus may include a biological signal generator configured to generate a biological signal by synthesizing the first biological signal and the second biological signal.

The first biological signal and the second biological signal may be displayed on a graph in relation to time, and the biological signal generator may generate the biological signal based on a sum of the first biological signal and the second biological signal based on at least one selected from a group including points on a time axis of the graph of the first biological signal.

The first biological signal and the second biological signal may be displayed on the graph in relation to time, and the biological signal generator may generate the biological signal based on the sum of the first biological signal and the second biological signal based on at least one selected from the group including a point at which a P wave of the first biological signal ends and a point at which a Q wave of the first biological signal starts among the points on the time axis of the graph of the first biological signal.

The first electrodes may contact the skin of the subject within a distance shorter than a distance between every two electrodes of a standard 12 leads, so that the first electrodes are relatively close to each other, and the second electrodes may contact the skin of the subject within a distance shorter than the distance between every two electrodes of the standard 12 leads, so that the first electrodes are relatively close to each other.

The characteristics of the contact parts of the first and second electrodes may be determined based on similarity between the electrical characteristic difference between the first electrodes and the electrical characteristic difference between the second electrodes.

The first and second unit measurers may be comprised in a pad.

The first and second electrodes may be arranged on a pad.

The electrical characteristic difference between the first electrodes may be a potential difference between the first electrodes, and the electrical characteristic difference between the second electrodes may be a potential difference between the second electrodes, and the biological signal generator may generate the biological signal based on a sum of the potential difference between the first electrodes and the potential difference between the second electrodes.

According to another aspect, a biological signal measuring method is provided. The biological signal measuring method includes receiving a first biological signal of a subject from a first unit measurer contacting the skin of the subject, receiving a second biological signal from a second unit measurer contacting the skin of the subject at a position different from positions of the first unit measurer, and generating a biological signal by synthesizing the first biological signal and the second biological signal.

The first unit measurer may measure the first biological signal of the subject based on an electrical characteristic difference between first electrodes contacting the skin of the subject, the second unit measurer may measure the second biological signal of the subject based on an electrical characteristic difference between second electrodes contacting the skin of the subject at positions different from those of the first electrodes, and a plurality of unit measurers may include at least the first unit measurer and the second unit measurer are arranged based on characteristics of contact parts of the first and second electrodes.

The first biological signal and the second biological signal may be displayed on a graph in relation to time, and the generating of the biological signal may include generating the biological signal based on a sum of the first biological signal and the second biological signal based on at least one selected from a group including points on a time axis of the graph of the first biological signal.

The first biological signal and the second biological signal may be displayed on the graph in relation to time, and the generating of the biological signal may include generating the biological signal based on the sum of the first biological signal and the second biological signal based on at least one selected from the group including a point at which a P wave of the first biological signal ends and a point at which a Q wave of the first biological signal starts among the points on the time axis of the graph of the first biological signal.

The first electrodes may contact the skin of the subject within a distance shorter than that between every two electrodes of a standard 12 leads, so that the first electrodes are relatively close to each other, and the second electrodes may contact the skin of the subject with a distance shorter than that between every two electrodes of the standard 12 leads to be relatively close to each other.

The characteristics of the contact parts of the first and second electrodes may be determined based on similarity between the electrical characteristic difference between the first electrodes and the electrical characteristic difference between the second electrodes.

the first and second unit measurers may be comprised in a pad.

The first and second electrodes may be arranged on a pad.

The electrical characteristic difference between the first electrodes may be a potential difference between the first electrodes, and the electrical characteristic difference between the second electrodes may be a potential difference between the second electrodes, and the generating of the biological signal may include generating the biological signal based on a sum of the potential difference between the first electrodes and the potential difference between the second electrodes.

A computer-readable recording medium may store a computer-readable program for executing the biological signal measuring method.

Other features and aspects may be apparent from the following detailed description, the drawings, and the claims.

Figure 1:
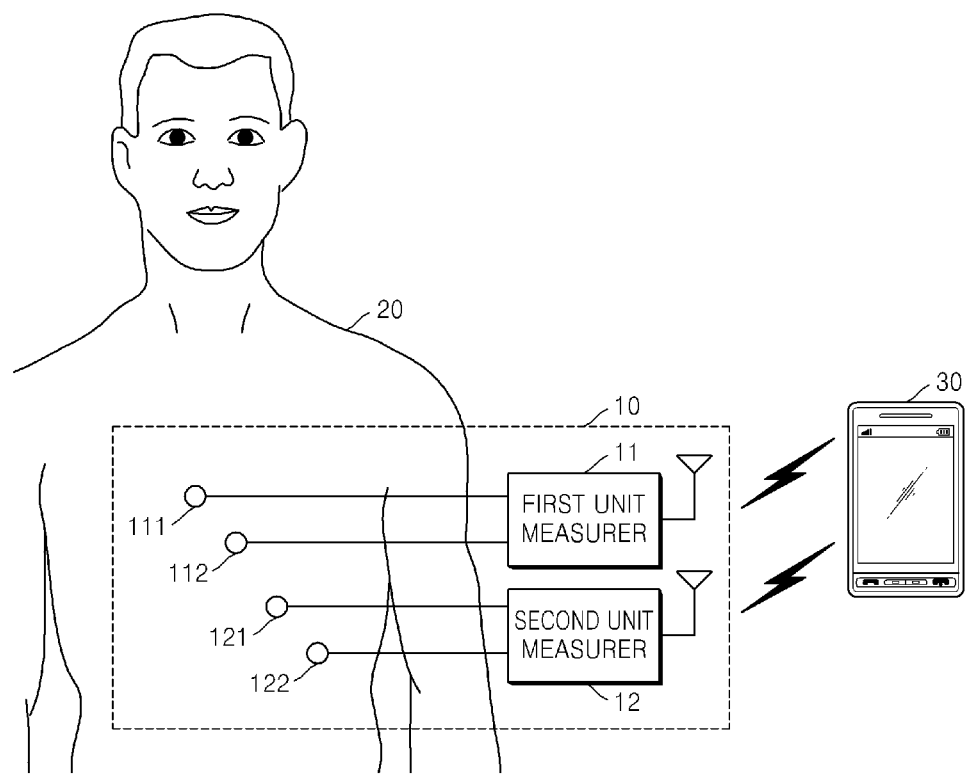
FIG. 1 is a block diagram illustrating a biological signal measuring apparatus according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

It is understood that the described example embodiments may have different forms and should not be construed as being limited to the descriptions set forth herein. Accordingly, the embodiments are merely described below, by referring to the figures, to explain aspects of the present description. For example, embodiments with respect to configurations for measuring a biological signal of a subject may be described for conciseness. However, it is understood that other general-use configurations may be provided besides the configurations for measuring a biological signal of a subject. For example, a configuration for displaying a biological signal of a subject on a screen or on paper may be added besides the configurations for measuring a biological signal of a subject so that a medical expert, such as a doctor, may interpret a biological signal.

FIG. 1 illustrates a biological signal measuring apparatus 10 according to an example embodiment.

Referring to FIG. 1, the biological signal measuring apparatus 10 may include a first unit measurer 11, first electrodes 111 and 112, a second unit measurer 12, and second electrodes 121 and 122. However, the biological signal measuring apparatus 10 illustrated in FIG. 1 is only an example embodiment, and it will be understood by those of ordinary skill in the art that various modifications may be performed based on the components shown in FIG. 1.

The first unit measurer 11 may measure a first biological signal of a subject 20 based on a difference between an electrical characteristic measured by the first electrodes 111 and 112 contacting the skin of the subject 20. The first electrodes 111 and 112 may perform electrical interfacing with the skin of the subject 20. Thus, the electrical characteristic difference between the first electrodes 111 and 112 may indicate a difference between an electrical characteristic corresponding to electrical interfacing between the first electrode 111 and the skin of the subject 20 and an electrical characteristic corresponding to electrical interfacing between the first electrode 112 and the skin of the subject 20. In general, these electrical characteristics may indicate electric potentials, and this electrical characteristic difference may indicate a potential difference. As a result, the first unit measurer 11 may measure the first biological signal based on a potential difference between the first electrodes 111 and 112 contacting different positions on the surface of the skin of the subject 20. Thus, the first biological signal may be measured because of an electric potential difference between different positions on the surface of the skin of the subject 20.

The second unit measurer 12 may measure a second biological signal of the subject 20 based on an electrical characteristic difference between the second electrodes 121 and 122 contacting the skin of the subject 20 at positions different from the positions of the first electrodes 111 and 112. The second electrodes 121 and 122 may also perform electrical interfacing with the skin of the subject 20. Thus, the second unit measurer 12 may measure the second biological signal based on a potential difference between the second electrodes 121 and 122 contacting different positions on the surface of the skin of the subject 20.

In general, the first electrodes 111 and 112 may be a pair of electrodes and the second electrodes 121 and 122 may be a pair of electrodes. However, the pair of first electrodes 111 and 112 and the pair of second electrodes 121 and 122 may each be replaced with a single electrode or more than two electrodes. In addition, the first electrodes 111 and 112 and the second electrodes 121 and 122 may each be a wet-type or dry-type electrode. The wet-type electrode may be a solid-type conductive electrode having a gel of an electrolyte component spread on and the gel contacts the skin of a subject. The dry-type electrode may be a solid-type conductive electrode that directly contacts the skin of a subject.

The first electrodes 111 and 112 may be arranged within a predetermined distance from each other so that the first electrodes 111 and 112 are relatively close to each other. In general, a distance between the first electrodes 111 and 112 contacting the skin of the subject 20 is shorter than a distance between every two electrodes of standard 12 leads. For example, the first electrodes 111 and 112 may be arranged within a distance of 2 cm from each other to be relatively close to each other. Likewise, the second electrodes 121 and 122 may be arranged within a predetermined distance from each other so that the second electrodes 121 and 122 are relatively close to each other. In general, a distance between the second electrodes 121 and 122 contacting the skin of the subject 20 is shorter than a distance between every two electrodes of standard 12 leads.

A plurality of unit measurers including at least the first unit measurer 11 and the second unit measurer 12 may be arranged on the skin of the subject 20 based on characteristics of contact parts of electrodes. In general, the characteristics of the contact parts may be determined based on similarity between the electrical characteristic difference between the first electrodes 111 and 112 and the electrical characteristic difference between the second electrodes 121 and 122. In this example, the electrical characteristic difference may be a potential difference.

In general, the unit measurers including the first unit measurer 11 and the second unit measurer 12 may be included in a pad. For example, this pad may be a patch-type pad, which contacts the skin of the subject 20. In general, the pad may include a first pad including the first measurer 11 and a second pad including the second measurer 12. In this case, the second pad may be located within a threshold distance from the first pad so that the second pad is relatively close to the first pad. In this example, the threshold distance may be 10 cm. However, the pad may be a single pad that includes both the first unit measurer 11 and the second unit measurer 12. In general, this pad may be formed of a nonconductive substance so that the pad does not affect the electrical interfacing between the electrodes and the skin of the subject 20. The nonconductive substance may be various substances, such as rubber, fiber, and plastic. However, according to another example embodiment, the pad may be formed of a conductive substance or a semiconductive substance.

The first unit measurer 11 and the second unit measurer 12 may be formed of a flexible circuit substrate to be included in the pad. In addition, the first unit measurer 11 and the second unit measurer 12 may be configured to be coupled to and decoupled from the pad.

The electrodes, for example, the first electrodes 111 and 112 and the second electrodes 121 and 122, may be arranged on the pad. In general, the first electrodes 111 and 112 may be arranged on the pad corresponding to the first unit measurer 11, and the second electrodes 121 and 122 may be arranged on the pad corresponding to the second unit measurer 12. For example, the pad may include a first pad and a second pad, wherein the first electrodes 111 and 112 are arranged on the first pad and the second electrodes 121 and 122 are arranged on the second pad. However, the pad may be a single pad on which both the first electrodes 111 and 112 and the second electrodes 121 and 122 may be arranged. In addition, the electrodes may be configured to be coupled to and decoupled from the pad. For example, the electrodes may be configured with a snap button to allow the electrodes to be coupled to and decoupled from the pad.

The first unit measurer 11 may process the first biological signal based on at least one signal processing, and the second unit measurer 12 may process the second biological signal based on at least one signal processing. In general, a signal processing may mean that a signal is extracted, delivered, or stored to obtain desired information or a signal is processed to monitor or control a system. Representative examples of a signal processing may include 1) a noise filtering operation in which noise is removed from a detected signal, 2) an amplifying operation in which a detected signal is amplified, 3) an Analog-to-Digital (A/D) converting operation in which an amplified analog signal is converted into a digital signal, and 4) a calculating operation in which a digital signal is calculated. Thus, the first unit measurer 11 and the second unit measurer 12 may each be implemented by an amplifier, an A/D converter, a calculator, and a noise filter for signal processings.

The first unit measurer 11 may transmit the first biological signal to a personal terminal 30. Likewise, the second unit measurer 12 may transmit the second biological signal to the personal terminal 30. In general, each of the first biological signal and the second biological signal may be transmitted to the personal terminal 30 through various wired and wireless communication channels. Thus, the first unit measurer 11 and the second unit measurer 12 may each include a wired and wireless communication module, and the wired and wireless communication channels may be configured to communicate with the personal terminal 30. In addition, the first biological signal and the second biological signal may be displayed by the personal terminal 30. For example, the first biological signal and the second biological signal may be displayed by a display unit included in the personal terminal 30. Examples of the personal terminal 30 may include various types of terminals, such as a cellular phone, a Personal Digital Assistant (PDA), and a Personal Computer (PC).

The personal terminal 30 may include a biological signal generator. In general, the biological signal generator may generate a biological signal by synthesizing the first biological signal and the second biological signal. In addition, the biological signal may be displayed by the personal terminal 30. For example, the biological signal may be displayed by the display unit included in the personal terminal 30.

Components of the biological signal measuring apparatus 10 shown in FIG. 1 will be described in more detail with reference to the drawings below.

Figure 2:
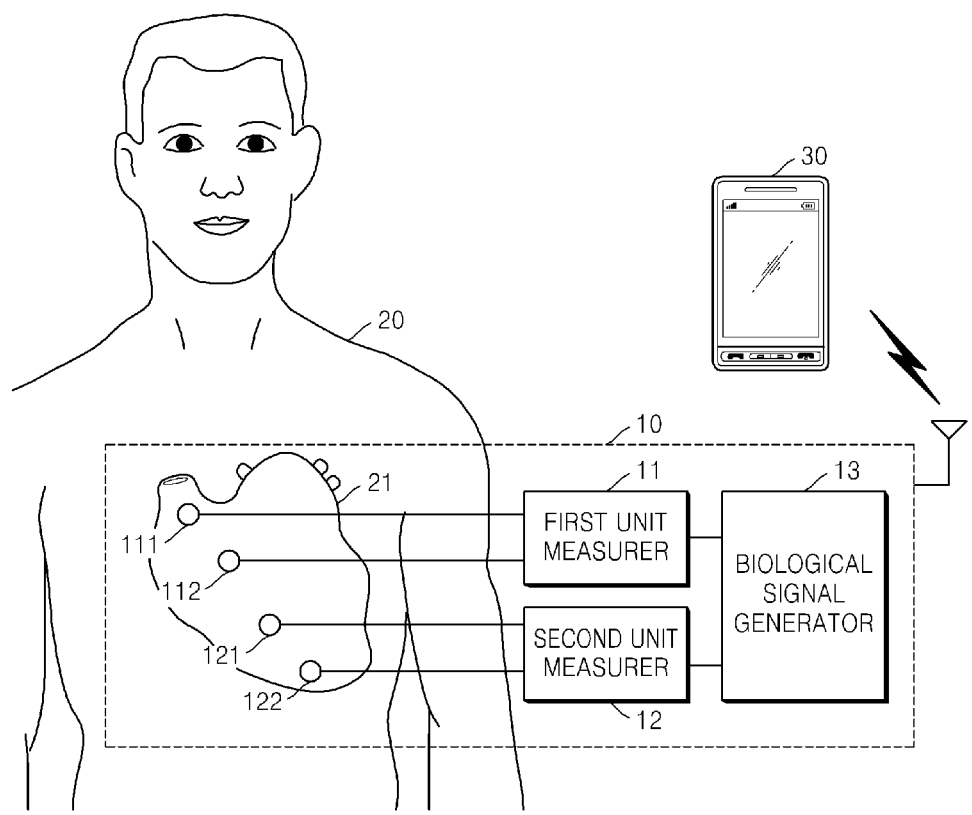
FIG. 2 is a block diagram illustrating the biological signal measuring apparatus according to another example embodiment.

FIG. 2 illustrates the biological signal measuring apparatus 10 according to another example embodiment. Referring to FIG. 2, the biological signal measuring apparatus 10 may include the first unit measurer 11, the first electrodes 111 and 112, the second unit measurer 12, the second electrodes 121 and 122, and a biological signal generator 13. The components of the biological signal measuring apparatus 10 shown in FIG. 2 other than the biological signal generator 13 may be the same as the components of the biological signal measuring apparatus 10 shown in FIG. 1. Thus, although omitted below, the contents described above for the biological signal measuring apparatus 10 shown in FIG. 1 may be applicable to the biological signal measuring apparatus 10 shown in FIG. 2.

The first unit measurer 11 may measure the first biological signal of the subject 20 from the electrical characteristic difference between the first electrodes 111 and 112 contacting the skin of the subject 20. The first electrodes 111 and 112 may perform electrical interfacing with the skin of the subject 20. In general, the first biological signal may be measured because of an electrical potential difference between different positions on the surface of the skin of the subject 20. Thus, the first biological signal may be measured by measuring the potential difference between the first electrodes 111 and 112. In other words, a voltage between the first electrodes 111 and 112. In general this potential difference may be measured by measuring an electrocardiogram (ECG) signal over time. However, the first biological signal may be measured by measuring an electrical potential at a predetermined point on the surface of the skin of the subject 20 based on a single electrode or measured by measuring a combination of points based on a plurality of electrodes.

A representative example of the first biological signal may be an ECG signal. An ECG is a graph obtained by measuring a potential difference between two predetermined positions on the outside of a heart 21 of the subject 20 to obtain a sum of action currents generated when ventricle muscles and atrium muscles contract. However, the example embodiment shown in FIG. 2 may be applied to other biological signals, such as 1) a brain wave signal and 2) an electromyogram (EMG) signal, which may be electrically detected from the torso of the subject 20.

Figure 3:
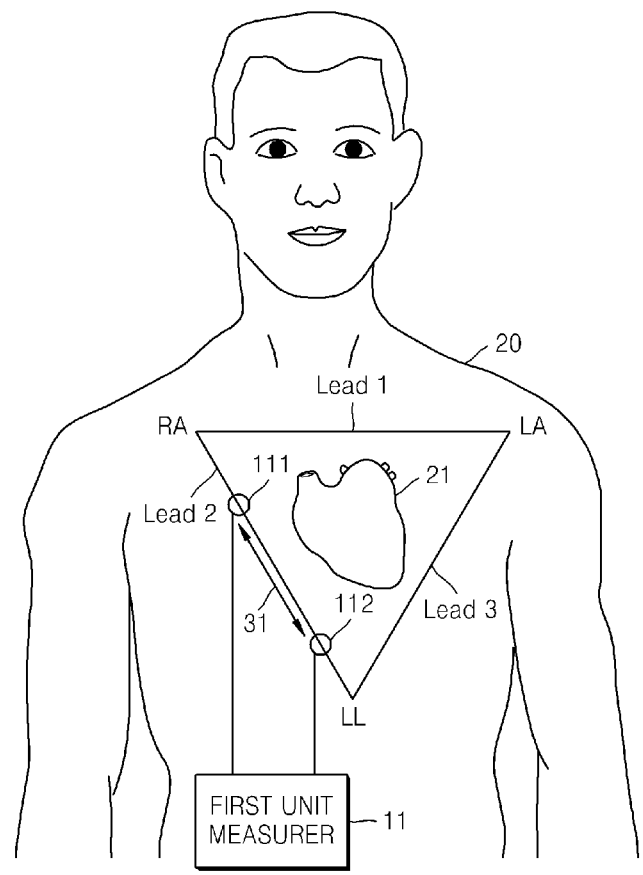
FIG. 3 is a configuration diagram illustrating first electrodes and a first unit measurer.

FIG. 3 illustrates the first electrodes 111 and 112 and the first unit measurer 11. As shown in FIG. 3, the first electrodes 111 and 112 1) may be located on the surface of the skin of the subject 20 and 2) may perform electrical interfacing with the skin of the subject 20. The first unit measurer 11 may detect electrical potentials of the surface of the skin from the first electrodes 111 and 112. The first unit measurer 11 may generate the first biological signal, based on the potential difference between the first electrodes 111 and 112. The first biological signal may vary and may repeatedly ascend and descend over time. In general, the first electrodes 111 and 112 for detecting the first biological signal may be defined as components of a lead. The lead may include a single electrode or at least a pair of electrodes to measure an ECG signal.

Standard 12 leads may be used to measure an ECG signal. The standard 12 leads may include 1) 3 standard limb leads for recording a front part of the heart 21, 2) 3 unipolar limb leads for recording a front part of the heart 21, and 3) 6 chest leads for recording a horizontal plane of the heart 21.

Referring to FIG. 3, the standard limb leads may include a lead 1, a lead 2, and a lead 3. Each of the lead 1, the lead 2, and the lead 3 may include measuring electrodes located at two of three vertices of an inverted triangle. For example, the lead 2 may have measuring electrodes at a point corresponding to a Right Arm (RA) on the surface of the skin of the subject 20 and a point corresponding to a Left Leg (LL) thereon. In this case, a potential difference between the measuring electrodes of the lead 2 may be detected as an ECG signal measured using the lead 2. Similarly, the lead 1 may have measuring electrodes at the point corresponding to the RA on the surface of the skin of the subject 20 and a point corresponding to a Left Arm (LA) thereon, and the lead 3 may have measuring electrodes at the point corresponding to the LA on the surface of the skin of the subject 20 and the point corresponding to the LL thereon.

As shown in FIG. 3, the first electrodes 111 and 112 may contact the skin of the subject 20 on a side of the inverted triangle including the lead 2. In this case, the first biological signal may be an ECG signal having a waveform similar to or related to the ECG signal detected based on the lead 2. The first electrodes 111 and 112 may contact the skin of the subject 20 based on a side of the inverted triangle including the lead 1 or the lead 3.

Figure 4:
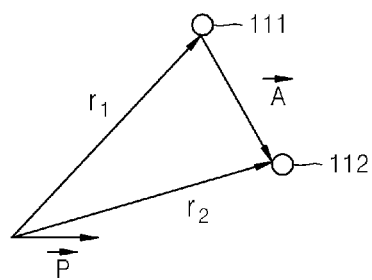
FIG. 4 is a diagram illustrating a relationship between a heart and the first electrodes used to calculate a potential difference between the first electrodes.

FIG. 4 illustrates a relationship between the heart 21 and the first electrodes 111 and 112 used to calculate the potential difference between the first electrodes 111 and 112. Referring to FIG. 4, the potential difference between the first electrodes 111 and 112 may be derived from 1) a dipole vector $\vec{P}$ representing the heart 21 considered as a source of a single or multiple electrical dipoles, 2) a position vector $r_1$ representing a distance from the heart 21 to the first electrode 111, 3) a position vector $r_2$ representing a distance from the heart 21 to the first electrode 112, and 4) a vector A ($\vec{A}$) between the first electrodes 111 and 112. However, to derive the potential difference between the first electrodes 111 and 112, it may be assumed that 1) the torso of the subject 20 is a uniform infinite conductor and 2) all myocardial cells of the heart 21 are the same distance away from each of the first electrodes 111 and 112.

When it is assumed that the heart 21 is a source of a single or multiple electrical dipoles, the potential difference between the first electrode 111 may be separated from the dipole vector $\vec{P}$ by the position vector $r_1$ and the first electrode 112 separated from the dipole vector $\vec{P}$ by the position vector $r_2$ may be calculated by Equation 1. In Equation 1, $v(r_2,r_1)$ denotes the potential difference between the first electrodes 111 and 112, r denotes a radius of a sphere including the first electrodes 111 and 112 as interior points of the sphere, and $\sigma_0$ denotes conductivity of the sphere.

$$v(r_2, r_1) = \frac{\vec{P} \cdot (r_2 - r_1)}{4\pi \cdot \sigma_0 r^3} \quad (1)$$

In addition, referring to Equation 1, since a difference between the position vector $r_2$ of the first electrode 112 and the position vector $r_1$ of the first electrode 111 is represented as the vector A ($\vec{A}$), Equation 1 may be expressed by Equation 2. In Equation 2, v denotes the potential difference between the first electrodes 111 and 112, vector P ($\vec{P}$) denotes the dipole vector, r denotes the radius of the sphere including the first electrodes 111 and 112 as interior points of the sphere, and $\sigma_0$ denotes the conductivity of the sphere.

$$v = \frac{\vec{P} \cdot \vec{A}}{4\pi\sigma_0 r^2} \quad (2)$$

Referring to Equation 2, the potential difference between the first electrodes 111 and 112 decreases as the vector A ($\vec{A}$) between the first electrodes 111 and 112 decreases. Vector A ($\vec{A}$) may represent the distance between the first electrodes 111 and 112, decreases. Accordingly, a magnitude of the first biological signal detected from the first electrodes 111 and 112 may decrease. Referring to FIG. 3, as a distance 31 between the first electrodes 111 and 112 decreases, the magnitude of the first biological signal output from the first unit measurer 11 may decrease. For example, when the distance 31 is 2 cm, the first biological signal detected from the first electrodes 111 and 112 may be an ECG signal having a magnitude and a quality lower than a magnitude and a quality of an ECG signal detected from the first electrodes 111 and 112 when the first electrodes 111 and 112 are located at the points corresponding to the RA and the LL, respectively. The ECG signal may be detected by lead 2 measurement. Here, the ECG signal having a lower quality may mean that a signal may not be useable by a clinician to determine whether the heart 21 is normal or abnormal.

Regardless of the relatively low magnitude and the relatively low quality, the first biological signal measured from the first electrodes 111 and 112 located relatively close to each other has various merits. First of all, the first electrodes 111 and 112 located relatively close to each other allow the biological signal measuring apparatus 10 to be miniaturized. Thus, a portable biological signal measuring apparatus that performs a low-power operation may be realized. For example, since the biological signal measuring apparatus 10 including the first electrodes 111 and 112 located relatively close to each other, for example, within 2 cm (the distance 31), may be manufactured to have a relatively small size, the biological signal measuring apparatus 10 may be always attached to the skin of the subject 20 to check whether the subject 20 is normal or abnormal. Furthermore, an ECG signal output from such a miniaturized ECG signal measuring apparatus may have enough quality for a user to determine whether his or her heart is normal or abnormal.

However, the first electrodes 111 and 112 may be separated from each other by a sufficient distance to detect the first biological signal of the subject 20 based on the voltage between the first electrodes 111 and 112. For example, distance of 2 cm may be sufficient.

Also, the first electrodes 111 and 112 may be arranged within a threshold distance from each other so that the first electrodes 111 and 112 may be close to each other. In general, the threshold distance may be determined by considering the size of the implementation of the biological signal measuring apparatus 10. For example, the threshold distance may be 4 cm to miniaturize the biological signal measuring apparatus 10. Alternatively, the threshold distance may be determined to be less than the distance between measuring electrodes of any one of the standard 12 leads. For example, the first electrodes 111 and 112 may contact the skin of the subject 20 within a distance from each other less than the distance between the measuring electrodes of the lead 2, so that the first electrodes 111 and 112 are close to each other.

The second unit measurer 12 may measure the second biological signal of the subject 20 based on the electrical characteristic difference between the second electrodes 121 and 122 contacting the skin of the subject 20 at positions different from those of the first electrodes 111 and 112. In this case, the second electrodes 121 and 122 may be separated from each other by a sufficient distance to detect the second biological signal of the subject 20 based on a voltage between the second electrodes 121 and 122. For example, a distance of 2 cm may be sufficient.

Also, the second electrodes 121 and 122 may be arranged to be within a threshold distance from each other, so that the second electrodes 121 and 122 are close to each other. In general, the threshold distance may be determined by considering the size of the manufacturing of the biological signal measuring apparatus 10. For example, the threshold distance may be 4 cm to miniaturize the biological signal measuring apparatus 10. Alternatively, the threshold distance may be determined to be less than the distance between the measuring electrodes of any one of the standard 12 leads. For example, the second electrodes 121 and 122 may contact the skin of the subject 20 by being close to each other by a distance from each other less than that between the measuring electrodes of the lead 2 to be close to each other.

The second unit measurer 12 may process the second biological signal based on at least one signal processing.

Referring to FIG. 3, the second electrodes 121 and 122 may also contact the skin of the subject 20 based on the side of the inverted triangle including the lead 2 similar with the first electrodes 111 and 112. Thus, the second electrodes 121 and 122 may also be an ECG signal having a waveform similar to or related to the ECG signal detected based on the lead 2. However, the second electrodes 121 and 122 may contact the skin of the subject 20 at positions different from the positions of the first electrodes 111 and 112.

Like the potential difference between the first electrodes 111 and 112, the potential difference between the second electrodes 121 and 122 may also be derived based on 1) the dipole vector P ($\vec{P}$) representing the heart 21, which is considered as a source of a single or multiple electrical dipoles, 2) a position vector $r_3$ representing a distance from the heart 21 to the second electrode 121, 3) a position vector $r_4$ representing a distance from the heart 21 to the second electrode 122, and 4) a vector B ($\vec{B}$) between the second electrodes 121 and 122. However, to derive the potential difference between the second electrodes 121 and 122, it may be assumed that 1) the torso of the subject 20 is a uniform infinite conductor and 2) all myocardial cells of the heart 21 are the same distance away from each of the second electrodes 121 and 122.

Figure 5:
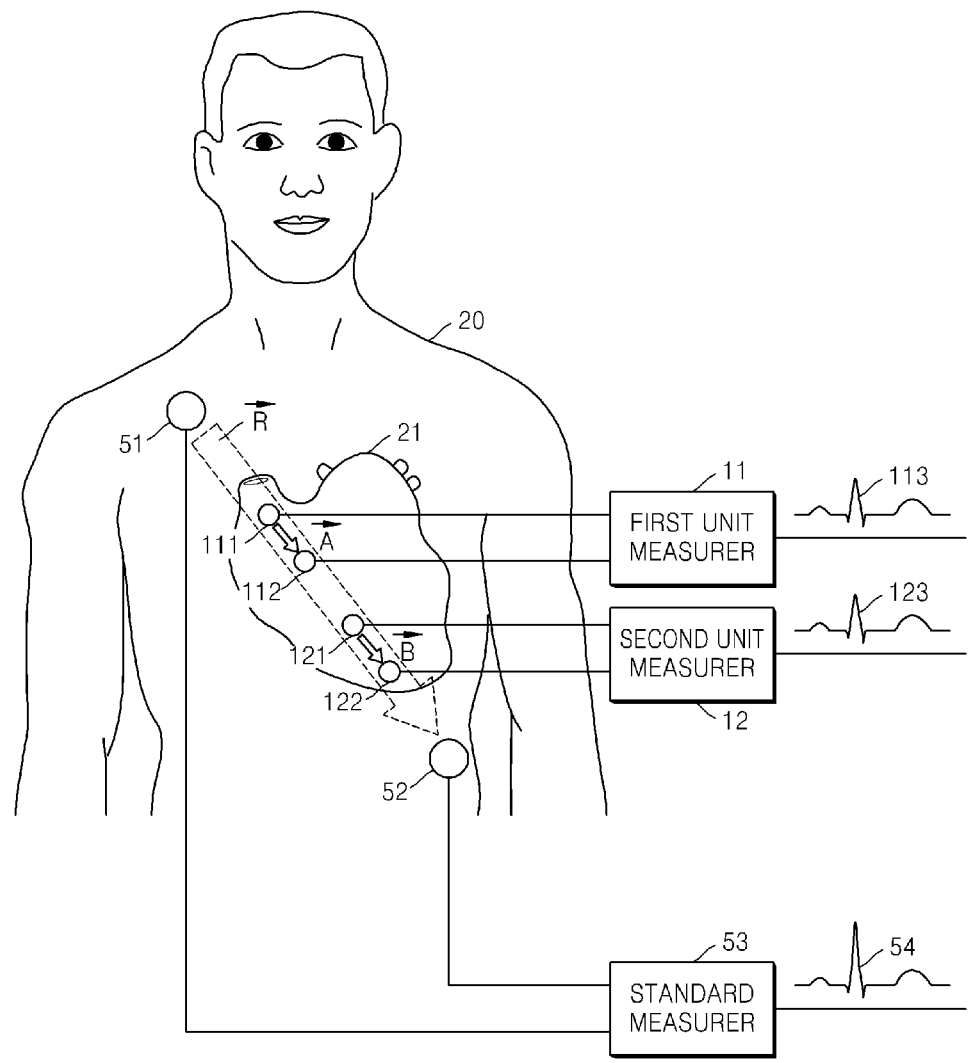
FIG. 5 is a configuration diagram illustrating the first electrodes, the first unit measurer, second electrodes, a second unit measurer, electrodes of a lead of standard 12 leads, and a standard measurer.

FIG. 5 illustrates the first electrodes 111 and 112, the first unit measurer 11, the second electrodes 121 and 122, the second unit measurer 12, electrodes 51 and 52 of the lead 2, and a standard measurer 53. Referring to FIG. 5, the standard measurer 53 may generate an ECG signal 54 by detecting a potential difference between the electrode 51 located at the point corresponding to the RA on the surface of the skin of the subject 20 and the electrode 52 located at the point corresponding to the LL thereon according to a method of measuring the ECG signal 54 by the lead 2 of the standard 12 leads. In general, the ECG signal 54 may be an ECG signal having a greater magnitude and a better quality than a magnitude and a quality of a first biological signal 113 or a magnitude and a quality of a second biological signal 123. In the example, the ECG signal having the better quality may mean that such a signal may be used by a clinician to determine whether the heart 21 is normal or abnormal. For example, the clinician may determine whether the subject 20 has an abnormal heart condition, such as arrhythmia, by using the ECG signal having the better quality.

Like the potential difference between the first electrodes 111 and 112 or the potential difference between the second electrodes 121 and 122, the potential difference between the electrodes 51 and 52 may also be derived based on 1) the dipole vector $\vec{P}$ representing the heart 21, which is considered as a source of a single or multiple electrical dipoles, 2) a position vector $r_{RA}$ representing a distance from the heart 21 to the electrode 51, 3) a position vector $r_{LL}$ representing a distance from the heart 21 to the electrode 52, and 4) a vector R ($\vec{R}$) between the electrodes 51 and 52. However, to derive the potential difference between the electrodes 51 and 52, it may be assumed that 1) the torso of the subject 20 is a uniform infinite conductor and 2) all myocardial cells of the heart 21 are the same distance away from each of the electrodes 51 and 52.

The second electrodes 121 and 122 may be located at positions different from the positions of the first electrodes 111 and 112. In general, the first electrodes 111 and 112 may be connected to the first unit measurer 11, and the second electrodes 121 and 122 may be connected to the second unit measurer 12. Thus, the second unit measurer 12 connected to the second electrodes 121 and 122 may be arranged with the first unit measurer 11 at a position different from the position of the first unit measurer 11 connected to the first electrodes 111 and 112. That is, a plurality of unit measurers including at least the first unit measurer 11 and the second unit measurer 12 may be arranged based on characteristics of contact parts of electrodes.

In general, the characteristics of contact parts of electrodes may be determined based on the similarity between the electrical characteristic difference between the first electrodes 111 and 112 and the electrical characteristic difference between the second electrodes 121 and 122. As described above, these electrical characteristic differences correspond with potential differences. Thus, the first unit measurer 11 and the second unit measurer 12 may be arranged based on the similarity between the electrical characteristic difference between the first electrodes 111 and 112 and the electrical characteristic difference between the second electrodes 121 and 122. In addition, the similarity between these electrical characteristic differences may be caused by a line of induction formed by electrodes on the surface of the skin of the subject 20. For example, when all of the first electrodes 111 and 112 and the second electrodes 121 and 122 are located on a line of induction formed by the electrodes 51 and 52 of the lead 2, there may be similarity in that the potential difference between the first electrodes 111 and 112 is a portion of a potential difference between the electrodes 51 and 52 and the potential difference between the second electrodes 121 and 122 is also a portion of the potential difference between the electrodes 51 and 52. This similarity will be described in more detail with reference to FIG. 6 below.

Figure 6:
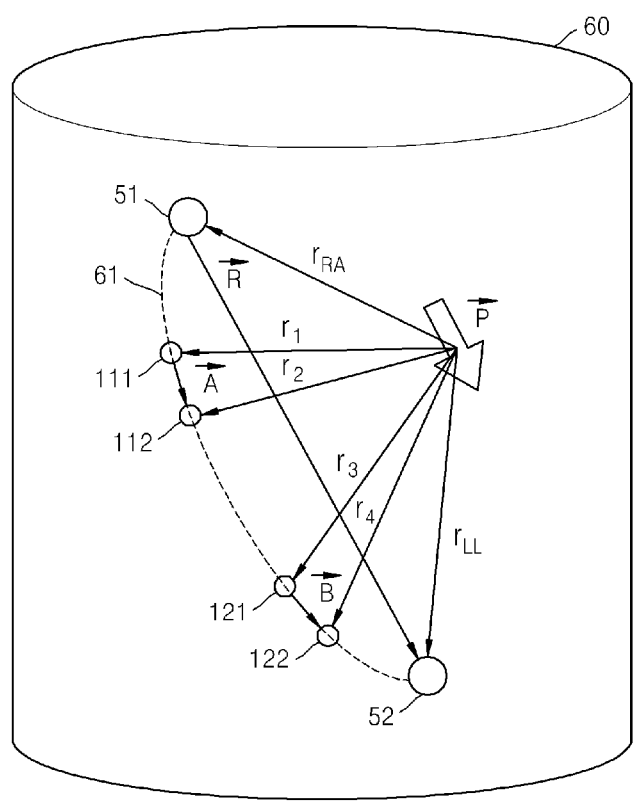
FIG. 6 is a diagram illustrating a relationship between an electrocardiogram (ECG) signal measured based on the lead of the standard 12 leads and a first biological signal and a second biological signal measured based on the biological signal measuring apparatus.

FIG. 6 illustrates a relationship between the ECG signal 54 measured based on the lead 2 of the standard 12 leads and the first biological signal 113 and the second biological signal 123 measured based on the biological signal measuring apparatus 10. Referring to FIG. 6, when the torso of the subject 20 is considered to be a cylinder, the potential difference between the electrodes 51 and 52 located on the surface of the skin of the subject 20 may be calculated by Equation 3. In Equation 3, $v_{LEAD2}$ denotes the potential difference between the electrodes 51 and 52, vector P ($\vec{P}$) denotes the dipole vector, $r_{RA}$ denotes the position vector from vector P ($\vec{P}$) to the electrode 51, $r_{LL}$ denotes the position vector from vector P ($\vec{P}$) to the electrode 52, and $\sigma_0$ denotes conductivity of a sphere including the electrodes 51 and 52 as interior points of the sphere. In addition, $(r_{LL}-r_{RA})^3$ may denote a value of the cube of a radius of the sphere.

$$v_{LEAD2} = \frac{\vec{P} \cdot (r_{LL} - r_{RA})}{4\pi\sigma_0 (r_{LL} - r_{RA})^3} \quad (3)$$

Likewise, as shown in FIG. 6, when the torso of the subject 20 is considered to be a cylinder, the potential difference between the first electrodes 111 and 112 may be calculated by Equation 4. In Equation 4, $v(r_2,r_1)$ denotes the potential difference between the first electrodes 111 and 112, vector P ($\vec{P}$) denotes the dipole vector, $r_1$ denotes the position vector from vector P ($\vec{P}$) to the first electrode 111, $r_2$ denotes the position vector from vector P ($\vec{P}$) to the first electrode 112, and $\sigma_0$ denotes conductivity of the sphere including the first electrodes 111 and 112 as interior points of the sphere. In addition, $(r_2-r_1)^3$ may denote a value of the cube of the radius of the sphere.

$$v(r_2, r_1) = \frac{\vec{P} \cdot (r_2 - r_1)}{4\pi\sigma_0 (r_2 - r_1)^3}$$

Comparing Equation 3 with Equation 4 with reference to FIG. 6, when the first electrodes 111 and 112 are located on a trajectory 61 formed by the electrodes 51 and 52 of the lead 2, the potential difference between the first electrodes 111 and 112 may be a portion of the potential difference between the electrodes 51 and 52. This is in accordance with the electromagnetic theory stating that an electric field is a conservative system. As a result, when 2N electrodes forming N leads shorter than a distance between the electrodes 51 and 52 of the lead 2 are arranged on the line of induction formed by the electrodes 51 and 52 of the lead 2, an arithmetic sum of potential differences measured from the N leads may be identical to $v_{LEAD\ 2}$, that is, the potential difference between the electrodes 51 and 52 of the lead 2.

The $v_{LEAD\ 2}$ may be represented by Equation 5. In Equation 5, $v_{LEAD\ 2}$ denotes the potential difference between the electrodes 51 and 52, vector P ($\vec{P}$) denotes the dipole vector, $r_{RA}$ denotes the position vector from vector P ($\vec{P}$) to the electrode 51, $r_{LL}$ denotes the position vector from vector P ($\vec{P}$) to the electrode 52, $E_{Pi}$ denotes a first electrode forming an $i^{th}$ lead, $E_{Ni}$ denotes a second electrode forming the $i^{th}$ lead, and $\sigma_0$ denotes conductivity of a sphere including the first and second electrodes as interior points of the sphere.

$$v_{LEAD2} = \frac{\vec{P} \cdot (r_{LL} - r_{RA})}{4\pi\sigma_0 (r_{LL} - r_{RA})^2} = \sum_{i=1}^{N} \frac{\vec{P} \cdot (E_{Pi} - E_{Ni})}{4\pi\sigma_0 (E_{Pi} - E_{Ni})^2} \quad (5)$$

However, as described above, Equation 5 may assume that the first electrodes 111 and 112 and the second electrodes 121 and 122 are located on the line of induction formed by the electrodes 51 and 52 of the lead 2. Thus, as described above, the contact positions of the second electrodes 121 and 122 on the surface of the skin of the subject 20 may be determined based on the similarity between the potential difference between the first electrodes 111 and 112, which varies based on the positions of the first electrodes 111 and 112, and the potential difference between the second electrodes 121 and 122, which varies based on the positions of the second electrodes 121 and 122. For example, all of the first electrodes 111 and 112 and the second electrodes 121 and 122 may be located on the line of induction formed by the electrodes 51 and 52 of the lead 2. However, these positions may be determined based on the lead 1, the lead 3, or any of the other leads. For example, if the first electrodes 111 and 112 are located on a line of induction formed by the measuring electrodes of the lead 1, the second electrodes 121 and 122 may also be located on the line of induction.

According to an example embodiment, the second unit measurer 12 may be located at a position different from a position of the first unit measurer 11 and the position of the second unit measurer 12 may be determined based on similarity between 1) a first vector determined from the positions of the first electrodes 111 and 112 and 2) a second vector determined from the positions of the second electrodes 121 and 122. For example, as shown in FIG. 5, the vector A ($\vec{A}$)

between the first electrodes 111 and 112 may be similar to or related to the vector R ($\vec{R}$) determined by the lead 2. Likewise, the vector B ($\vec{B}$) between the second electrodes 121 and 122 may also be similar to or related to the vector R ($\vec{R}$) determined by the lead 2. As a result, the vector A ($\vec{A}$) and the vector B ($\vec{B}$) may also be similar to or related to each other. Thus, if the positions of the first electrodes 111 and 112 are determined to derive the vector A ($\vec{A}$) in relation to the vector R ($\vec{R}$), the positions of the second electrodes 121 and 122 may also be determined to derive the vector B ($\vec{B}$) in relation to the vector R ($\vec{R}$).

The biological signal generator 13 may generate a biological signal by synthesizing the first biological signal 113 and the second biological signal 123. The first biological signal 113 and the second biological signal 123 may be displayed on a graph in relation to time. In general, the biological signal generator 13 may generate the biological signal based on a sum of the first biological signal 113 and the second biological signal 123 based on at least one selected from the group consisting of points on a time axis of the graph of the first biological signal 113.

As described above, the electrical characteristic difference between the first electrodes 111 and 112 may be the potential difference between the first electrodes 111 and 112, and the electrical characteristic difference between the second electrodes 121 and 122 may be the potential difference between the second electrodes 121 and 122. Thus, the biological signal generator 13 may generate the biological signal based on a sum of the potential difference between the first electrodes 111 and 112 and the potential difference between the second electrodes 121 and 122. In other words, the biological signal generator 13 may temporally synchronize the first biological signal 113 and the second biological signal 123, synthesize the potential difference between the first electrodes 111 and 112 and the potential difference between the second electrodes 121 and 122 at each of time points, and generate the biological signal based on the synthesized potential difference. In this case, the first biological signal 113 may be based on the potential difference between the first electrodes 111 and 112 and the second biological signal 123 may be based on the potential difference between the second electrodes 121 and 122. In addition, the first biological signal 113 and the second biological signal 123 may be represented on a graph to illustrate a variance of each potential difference with respect to time.

The biological signal generator 13 may transmit the biological signal to the personal terminal 30. In general, the biological signal may be transmitted to the personal terminal 30 through various wired and wireless communication channels. Thus, the biological signal generator 13 may include a wired and wireless communication module. In addition, the biological signal may be displayed by the personal terminal 30. For example, the biological signal may be displayed by a display unit included in the personal terminal 30.

The biological signal generator 13 may process the biological signal based on at least one signal processing. Thus, the biological signal generator 13 may be implemented by an amplifier, an A/D converter, a calculator, and a noise filter for signal processings.

Figure 7:
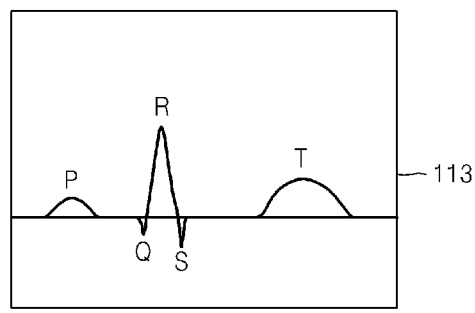
FIG. 7 is a diagram illustrating a relationship among the first biological signal, the second biological signal, and the ECG signal.
Figure 7:
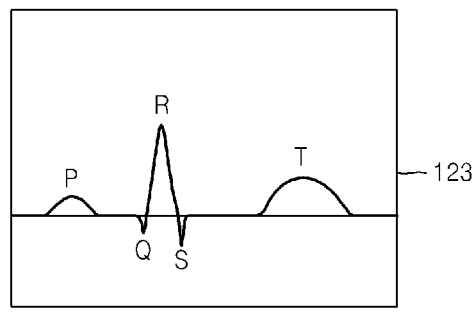
Figure 7:
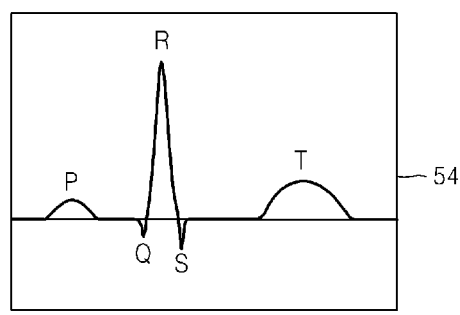

FIG. 7 illustrates a relationship among the first biological signal 113, the second biological signal 123, and the ECG signal 54. Referring to FIG. 7, the biological signal generator 13 may generate the biological signal based on the sum of the first biological signal 113 and the second biological signal 123 based on at least one selected from the group consisting of points on the time axis of the graph of the first biological signal 113. For example, the biological signal generator 13 may generate the biological signal based on the sum of the first biological signal 113 and the second biological signal 123. The sum may be based on at least one point selected from a group including a point at which a P wave of the first biological signal 113 ends and a point at which a Q wave of the first biological signal 113 starts among the points on the time axis of the graph of the first biological signal 113. In this case, the biological signal generator 13 may generate the biological signal based on a refractory period between the P wave and the Q wave. However, the biological signal generator 13 may generate the biological signal based on a point at which the P wave starts, a point at which the Q wave ends, a point at which an R wave starts, a point at which the R wave ends, a point at which an S wave starts, a point at which the S wave ends, a point at which a T wave starts, a point at which the T wave ends, and intervals obtained by combining the points among the points on the time axis of the graph of the first biological signal 113.

The biological signal may be an ECG signal having a magnitude and a quality similar to those of the ECG signal 54 measured by the lead 2. Thus, the biological signal may be used by a clinician to determine whether the heart 21 is normal or abnormal. Through this, the biological signal measuring apparatus 10 according to an example embodiment may provide not only a portable biological signal measuring service having a low-power operation but may also allow an ECG signal having an enhanced magnitude and an enhanced quality that allows the ECG signal to be used by a clinician.

In general, an ECG signal may include the P wave, the Q wave, the R wave, the S wave, and the T wave sequentially reflecting an electrical process of depolarization and repolarization of the myocardium. Thus, in the first biological signal 113 and the second biological signal 123, the P wave, the Q wave, the R wave, the S wave, and the T wave may be repeatedly formed.

Figure 8:
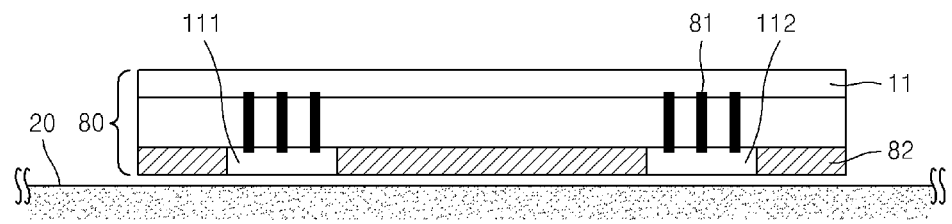
FIG. 8 is a side view illustrating the first unit measurer according to an example embodiment.

FIG. 8 illustrates a side view of the first unit measurer 11 according to an example embodiment. Referring to FIG. 8, the first unit measurer 11 may be included in a pad 80. However, the first unit measurer 11 may instead contact one side of the pad 80. In addition, the first electrodes 111 and 112 may be arranged in the pad 80 within a predetermined distance from each other. The first electrodes 111 and 112 may be connected to the first unit measurer 11 through an auxiliary connection device 81. Through the auxiliary connection device 81, the first unit measurer 11 may detect the potential difference between the first electrodes 111 and 112 contacting the skin of the subject 20 through an electrode support and measure the first biological signal 113 based on the detected potential difference. In addition, as described above, a gel of an electrolyte component may be spread on the first electrodes 111 and 112. In this case, the gel may support electrical interfacing between the skin of the subject 20 and the first electrodes 111 and 112 by contacting the skin of the subject 20. Alternatively, an adhesive gel 82 may be spread around the first electrodes 111 and 112 to adhere the first electrodes 111 and 112 to the skin of the subject 20. In this case, the adhesive gel 82 may be formed with 1) nontoxic silicon to prevent the first electrodes 111 and 112 from separating from the skin of the subject 20 due to sweat of the subject 20 or 2) an alien substance.

Figure 9:
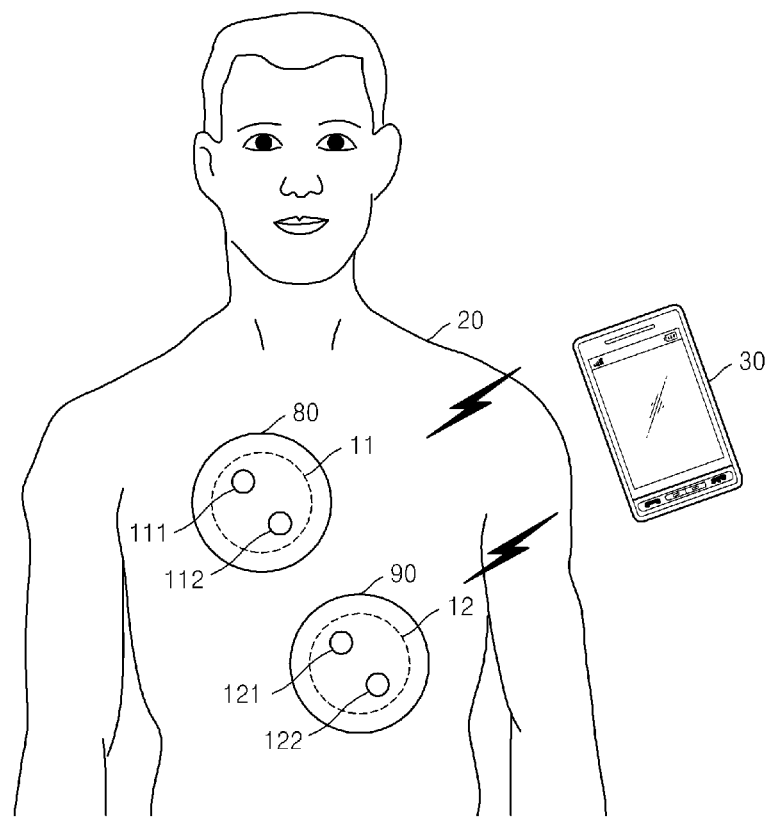
FIG. 9 is a configuration diagram illustrating a biological signal measuring apparatus according to an example embodiment.

FIG. 9 illustrates a configuration diagram of a biological signal measuring apparatus according to an example embodiment. Referring to FIG. 9, the first unit measurer 11 included in the pad 80 as a first pad may measure the first biological signal of the subject 20 from the electrical characteristic difference between the first electrodes 111 and 112 contacting the skin of the subject 20 and transmit the first biological signal to the personal terminal 30. Also, the second unit measurer 12 included in a second pad 90 may measure the second biological signal of the subject 20 from the electrical characteristic difference between the second electrodes 121 and 122 contacting the skin of the subject 20 and transmit the second biological signal to the personal terminal 30. The first unit measurer 11 included in the first pad 80 and the second unit measurer 12 included in the second pad 90 may be arranged based on characteristics of contacting parts of the first electrodes 111 and 112 and the second electrodes 121 and 122. The personal terminal 30 may generate the biological signal by synthesizing the first biological signal and the second biological signal and display the biological signal. Since contents not described in FIG. 9 may be easily derived by those of ordinary skill in the art from the contents described in FIGS. 1 to 8, they are omitted.

Figure 10:
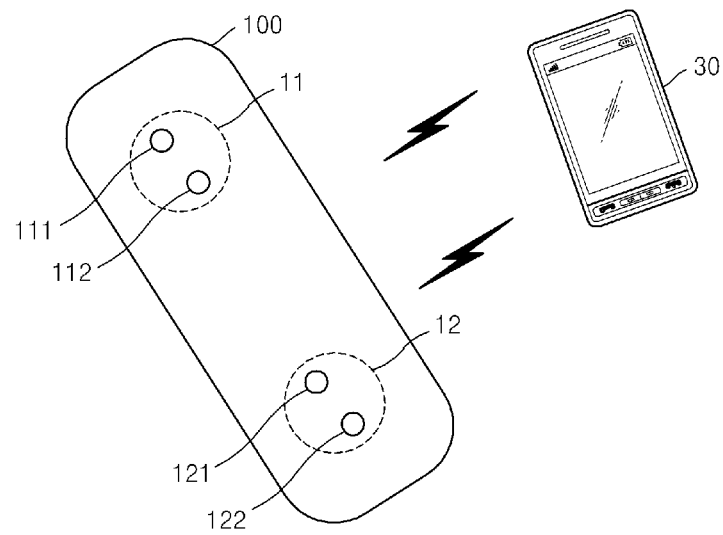
FIG. 10 is a configuration diagram illustrating a biological signal measuring apparatus according to another example embodiment.

FIG. 10 illustrates a configuration diagram of a biological signal measuring apparatus according to another example embodiment. Referring to FIG. 10, the first unit measurer 11 included in a pad 100 may measure the first biological signal of the subject 20 from the electrical characteristic difference between the first electrodes 111 and 112 contacting the skin of the subject 20 and transmit the first biological signal to the personal terminal 30. Likewise, the second unit measurer 12 included in the pad 100 may measure the second biological signal of the subject 20 from the electrical characteristic difference between the second electrodes 121 and 122 contacting the skin of the subject 20 and transmit the second biological signal to the personal terminal 30. Here, the first unit measurer 11 and the second unit measurer 12 both included in the pad 100 may be arranged based on the characteristics of the contacting parts of the first electrodes 111 and 112 and the second electrodes 121 and 122. The personal terminal 30 may generate the biological signal by synthesizing the first biological signal and the second biological signal and display the biological signal. Since contents not described in FIG. 10 may be easily derived by those of ordinary skill in the art from the contents described in FIGS. 1 to 8, they are omitted.

Figure 11:
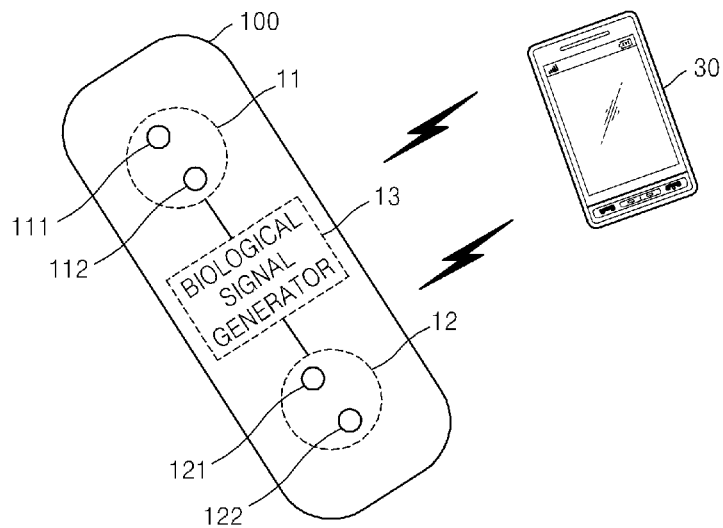
FIG. 11 is a configuration diagram illustrating a biological signal measuring apparatus according to another example embodiment.

FIG. 11 illustrates a configuration diagram of a biological signal measuring apparatus according to another example embodiment. Referring to FIG. 11, the first unit measurer 11 included in the pad 100 may measure the first biological signal of the subject 20 from the electrical characteristic difference between the first electrodes 111 and 112 contacting the skin of the subject 20. Likewise, the second unit measurer 12 included in the pad 100 may measure the second biological signal of the subject 20 from the electrical characteristic difference between the second electrodes 121 and 122 contacting the skin of the subject 20. The biological signal generator 13 included in the same pad 100 may generate the biological signal by synthesizing the first biological signal and the second biological signal and transmit the biological signal to the personal terminal 30. Here, the first unit measurer 11 and the second unit measurer 12 included in the same pad 100 may be arranged based on the characteristics of the contacting parts of the first electrodes 111 and 112 and the second electrodes 121 and 122. The personal terminal 30 may display the biological signal received from the biological signal generator 13. Since contents not described in FIG. 11 may be easily derived by those of ordinary skill in the art from the contents described in FIGS. 1 to 8, they are omitted.

Figure 12:
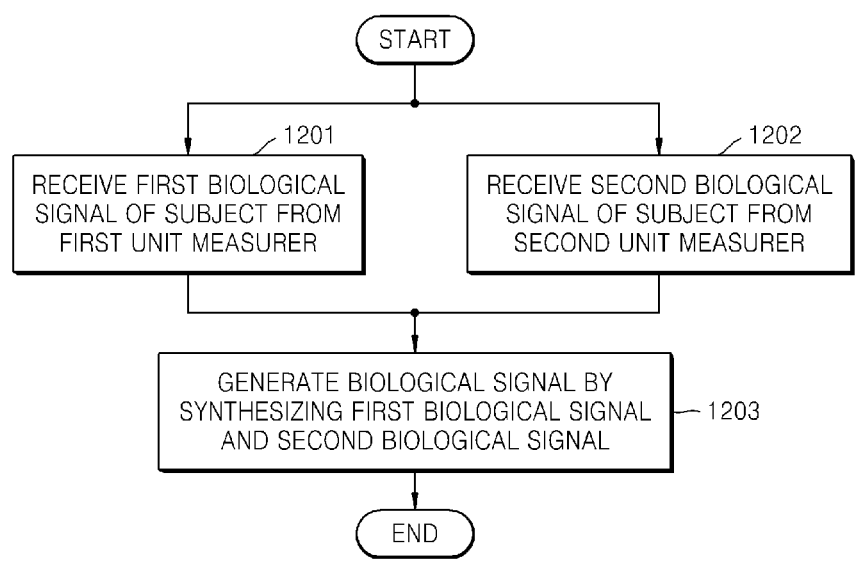
FIG. 12 is a flowchart illustrating a biological signal measuring method according to an example embodiment.

FIG. 12 illustrates a flowchart of a biological signal measuring method according to an example embodiment. The biological signal measuring method shown in FIG. 12 includes operations sequentially performed by the biological signal measuring apparatus 10 shown in FIG. 2. Thus, although omitted below, the contents described with respect to the biological signal measuring apparatus 10 shown in FIG. 2 are applied to the biological signal measuring method shown in FIG. 12.

In operation 1201, the biological signal generator 13 receives the first biological signal of the subject 20 from the first unit measurer 11 contacting the skin of the subject 20. In operation 1202, the biological signal generator 13 receives the second biological signal of the subject 20 from the second unit measurer 12 contacting the skin of the subject 20 at a position different from that of the first unit measurer 11. In operation 1203, the biological signal generator 13 generates the biological signal by synthesizing the first biological signal and the second biological signal.

However, a biological signal measuring method according to another example embodiment may include operations 1201 and 1202. Thus, in operation 1201, the biological signal generator 13 receives the first biological signal of the subject 20 from the first unit measurer 11 contacting the skin of the subject 20. In operation 1202, the biological signal generator 13 receives the second biological signal of the subject 20 from the second unit measurer 12 contacting the skin of the subject 20 at a position different from that of the first unit measurer 11. In addition, although omitted below, the contents described with respect to the biological signal measuring apparatus 10 shown in FIG. 1 are applied to the biological signal measuring method including operations 1201 and 1202.

According to the embodiments described above, an ECG measuring service capable of significantly increasing a magnitude and quality of an ECG signal by combining two or more signals while being portable and having low-power driving by being manufactured in a small size may be provided.

As described above, the first unit measurer 11, the second unit measurer 12, and the biological signal generator 13 may be implemented by an amplifier, an A/D converter, a calculator, and a noise filter.

As described above, according to the one or more of the above example embodiments, by generating a biological signal finally output by synthesizing a plurality of biological signals received from a plurality of unit measurers, a high quality and clinically usable biological signal may be measured while maintaining portability and convenience.

The biological signal measuring methods according to the embodiments shown in FIG. 12 may be written as computer programs and may be implemented in general-use digital computers that execute the programs using a computer readable recording medium. Examples of the computer readable recording medium are magnetic storage media (e.g., ROM, floppy disks, hard disks, etc.) and optical recording media (e.g., CD-ROMs, or DVDs).

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A biological signal measuring apparatus comprising:
   a first unit measurer configured to measure a first biological signal of a subject based on an electrical characteristic difference between first electrodes contacting the skin of the subject;
   a second unit measurer configured to measure a second biological signal of the subject based on an electrical characteristic difference between second electrodes contacting the skin of the subject at positions different from positions of the first electrodes; and
   a biological signal generator configured to generate a biological signal by arithmetically summing the measured first and second biological signals based on points on a time axis of a graphical display of the first biological signal or intervals obtained by combining the points, wherein:
   the first unit measurer and the second unit measurer are arranged based on characteristics of contact parts of the first and second electrodes,
   the first electrodes and the second electrodes are located on a line of induction,
   the first and second biological signals are synchronized in time during the summing such that the sum of their potentials is greater than the potential of either the first biological signal or second biological signal,
   the points include at least one of a point at which a P wave starts, a point at which the P wave ends, a point at which a Q wave starts, a point at which the Q wave ends, a point at which a R wave starts, a point at which the R wave ends, a point at which a S wave starts, a point at which the S wave ends, a point at which a T wave starts, and a point at which the T wave ends, and
   the first and second biological signals are further based on intervals obtained by combining the points among the points on a time axis of a graph of the first biological signal.

2. The biological signal measuring apparatus of claim 1, wherein
   the first electrodes contact the skin of the subject within a distance of 2 cm of each other, and
   the second electrodes contact the skin of the subject within a distance of 2 cm of each other.

3. The biological signal measuring apparatus of claim 1, wherein the characteristics of the contact parts of the first and second electrodes are determined based on similarity between the electrical characteristic difference between the first electrodes and the electrical characteristic difference between the second electrodes.

4. The biological signal measuring apparatus of claim 1, further comprising a pad that comprises the first and second unit measurers.

5. The biological signal measuring apparatus of claim wherein
   the electrical characteristic difference between the first electrodes is a potential difference between the first electrodes, and the electrical characteristic difference between the second electrodes is a potential difference between the second electrodes, and
   the biological signal generator generates the biological signal based on the sum of the potential difference between the first electrodes and the potential difference between the second electrodes.

6. A biological signal measuring method comprising:
   receiving a first biological signal of a subject from a first unit measurer contacting the skin of the subject;
   receiving a second biological signal from a second unit measurer contacting the skin of the subject at a position different from the position of the first unit measurer; and
   generating a biological signal by arithmetically summing the measured first biological signal and the second biological signal based on points on a time axis of a graphical display of the first biological signal or intervals obtained by combining the points, wherein
   the first and second biological signals are synchronized in time during the summing such that the sum of their potentials is greater than the potential of either the first biological signal or second biological signal,
   the points includes at least one of a point at which a P wave starts, a point at which the P wave ends, a point at which a Q wave starts, a point at which the Q wave ends, a point at which a R wave starts, a point at which the R wave ends, a point at which a S wave starts, a point at which the S wave ends, a point at which a T wave starts, and a point at which the T wave ends,
   the first and second biological signals are further based on intervals obtained by combining the points among the points on a time axis of a graph of the first biological signal,
   the first unit measurer measures the first biological signal of the subject based on an electrical characteristic difference between first electrodes contacting the skin of the subject,
   the second unit measurer measures the second biological signal of the subject based on an electrical characteristic difference between second electrodes contacting the skin of the subject at positions different from those of the first electrodes the first unit measurer and the second unit measurer are arranged based on characteristics of contact parts of the first and second electrodes, and the first electrodes and the second electrodes are located on a line of induction.

7. The biological signal measuring method of claim 6, wherein the first electrodes contact the skin of the subject within a distance of 2 cm of each other, and the second electrodes contact the skin of the subject with a distance of 2 cm of each other.

8. The biological signal measuring method of claim 6, wherein the characteristics of the contact parts of the first and second electrodes are determined based on similarity between the electrical characteristic difference between the first electrodes and the electrical characteristic difference between the second electrodes.

9. The biological signal measuring method of claim 6, wherein a pad comprises the first and second unit measurers.

10. The biological signal measuring method of claim 6, wherein the electrical characteristic difference between the first electrodes is a potential difference between the first electrodes, and the electrical characteristic difference between the second electrodes is a potential difference between the second electrodes, and the generating of the biological signal comprises generating the biological signal based on the sum of the potential difference between the first electrodes and the potential difference between the second electrodes.

11. A non-transitory computer-readable recording medium storing a computer-readable program for executing the biological signal measuring method of claim 6.

* * * * *